United States Patent [19]

Nishii et al.

[11] 4,011,219

[45] Mar. 8, 1977

[54] PHTHALAZINE DERIVATIVES AND SALTS THEREOF

[75] Inventors: Yasuho Nishii; Shun-ichi Hata; Kiyoshige Wakabayashi; Koji Mizuno, Tokyo; Akio Yoshida; Minoru Shindo, all of Tokyo, Japan

[73] Assignee: Chugai Seiyaku Kabushiki Kaisha, Tokyo, Japan

[22] Filed: Mar. 28, 1975

[21] Appl. No.: 562,920

[52] U.S. Cl. ............................ 260/250 P; 424/250
[51] Int. Cl.² ....................................... C07D 237/32
[58] Field of Search ................................ 260/250 P

[56] References Cited

UNITED STATES PATENTS 3,497,512  2/1970  Hofer et al. ............... 260/250 P

FOREIGN PATENTS OR APPLICATIONS 1,100,911  1/1968  United Kingdom ............ 260/250 P

OTHER PUBLICATIONS

Theilheimer; Synthetic Methods of Org. Chem. vol. 18, 542 (1961).

Theilheimer; Synthetic Methods of Org. Chem. vol. 12, 483 (1956).

Omote et al; Bull. Chem. Soc. Jap. vol. 40 pp. 1693–1695 (1967).

*Primary Examiner*—Raymond V. Rush
*Assistant Examiner*—Mary C. Vaughn
*Attorney, Agent, or Firm*—Browdy and Neimark

[57] ABSTRACT

Phthalazine derivatives represented by the formula

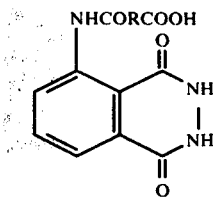

and salts thereof which are useful for a luminescence immuno assay, or a process for preparing the same are disclosed.

3 Claims, No Drawings

PHTHALAZINE DERIVATIVES AND SALTS THEREOF

This invention relates to a novel phthalazine derivative represented by the formula

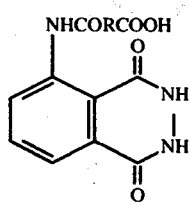

wherein R is a lower alkylene and a salt thereof, and to a process for preparing the derivative and the salt thereof.

The inventors of this invention had studied for a long time in order to develop an excellent chemiluminescent substance. It was found that the compounds represented by the formula above have chemiluminescence ability comparable to luminol, a well known compound as chemiluminescent substance. Furthermore, the terminal carboxyl radical of the compounds of the present invention can be easily bound with an amino radical of, for example, protein.

These properties of the phthalazine derivative of the present invention are very important for a luminescence immuno assay of a minor component in a living body.

That is, the compound represented by the formula I is bound with a peptide hormone such as insulin, growth hormone, glucagon, albumin or the like in a conventional way to obtain a luminescent substance-labeled hormone. Since the labeled hormone still maintains luminescence ability, the amount of hormone in the test sample can be accurately determined in terms of luminescent level of the luminescence labeled-hormone without using a radioactive substance which is a marker for the conventional immuno assay for the hormone.

This invention will be more specifically explained by reference to a case in which insulin is used. The luminescent substance-labeled insulin mentioned above and an antibody against insulin (antiinsulin) are added in predetermined amounts respectively to a sample containing insulin, so that the labeled insulin and non-labeled insulin are competitively reacted with the antibody to be bound with it. Therefore, the amount of the labeled insulin bound with the antiinsulin is reduced as the amount of insulin in the sample (non-labeled insulin) increases. In other words, the amount of labeled insulin-antiinsulin complex (B) is reduced and, at the same time, the amount of free form of labeled insulin (F) which is not bound with antiinsulin increases.

The resulting complex (B) and the free form of labeled insulin (F) are separated from the reaction system in an appropriate conventional way such as centrifugation, filtration, column-chromatography or the like, and then the luminescence ability of each of the substances (B) and (F) is determined to calculate the value B/B+F. On the other hand, the standard curve is prepared by using several samples each of which contains a predetermined amount of non-labeled insulin to obtain the values, B/B+F and plotting the values. The standard curve is applied to the value obtained from a test sample to be assayed to determine the amount of insulin therein.

In accordance with this invention, the compound represented by the formula I may be prepared by reacting 5-amino-2,3-dihydro-1,4-phthalazinedione with a dicarboxylic acid.

The dicarboxylic acids which may be used in the reaction include, for example, malonic acid, succinic acid, glutaric acid, adipic acid and suberic acid, and if necessary, these compounds may be used in the form of their functional derivative e.g. anhydride, dihalide, monoester-monohalide and the like.

The reaction is advantageously carried out in a solvent under acidic condition, and especially, it can be effected in acetic acid under reflux to obtain the object compound in a highly improved yield.

In the last case, since the object compound is precipitated at the completion of the reaction, the precipitates are filtered out and dissolved in an aqueous ammonia. The solution is made weakly alkaline and treated with activated carbon, and the pH of the solution is adjusted to around neutral value by the addition of an acid to obtain the object compound as an ammonium salt.

The ammonium salt may be optionally converted to the corresponding free acid by treatment with acetic acid.

EXAMPLE 1

In 50 ml of glacial acetic acid were suspended 5.3 g of 5-amino-2,3-dihydro-1,4-phthalazinedione and 3 g of succinic anhydride and the suspension was heated to reflux while stirring with a magnetic stirrer. About 10 – 20 minutes after the starting of the reflux, the suspended materials were dissolved to form a dark brown uniform solution. The continuation of heating gradually precipitated a brown reaction product from the solution. The reaction was terminated one hour after starting the reflux, then the reaction mixture was cooled and filtered to obtain the crude product, brown in color, which decomposed at about 270° C.

The crude product was dissolved in 1% ammonia aqueous solution and after the treatment of activated carbon, the pH of the solution was adjusted to 7 by the addition of 5% acetic acid aqueous solution to precipitate the crystals. The crystals were separated from the reaction mixture by filtration and washed with water to obtain the ammonium salt of the object compound as white crystals. The crystals were dissolved in 1% ammonia aqueous solution and the pH of the solution was adjusted to 3 or lower to precipitate white crystals which were recovered by filtration to obtain 3 g (as dry materials) of 5-succinoamido-2,3-dihydro-1,4-phthalazinedione, which was sintered at a temperature between 290° – 293° C and decomposed at 330° C.

Analysis:

Calcd. for $C_{12}H_{11}N_3O_5$: C, 51.99; H, 4.00; N, 15.16 (%)

Found: C, 51.73; H, 3.85; N, 15.04 (%)

EXAMPLE 2

In 100 ml of glacial acetic acid containing 5 ml of pyridine were suspended 5.3 g of 5-amino-2,3-dihydro-1,4-phthalazinedione and 3.1 g of glutaric anhydride and the suspension was heated under reflux while stirring. About 30 minutes after the starting of the reflux, the suspended materials were dissolved to form a solution and after about 30 additional minutes the reaction product started to precipitate from the solution. The reaction mixture was cooled about 30 minutes after the reaction was started to obtain crude brown product. The crude product was treated in a way similar to that of Example 1 to obtain 4.2 g of 5-glutaramido-2,3-dihydro-1,4-phthalazinedione as white powdery crystals which were molten at a temperature between 295° – 297° C.

Analysis:

Calcd.: for $C_{13}H_{13}N_3O_5$: C, 53.61; H, 4.50; N, 14.43 (%)

Found: C, 53.32; H, 4.24; N, 14.19 (%)

What is claimed is:

1. A compound represented by the formula

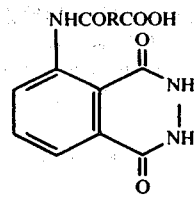

wherein R represents an alkylene having 1-6 carbon atoms, or a salt thereof.

2. The compound as set forth in claim 1 wherein said alkylene is ethylene.

3. A compound as set forth in claim 1 wherein said alkylene is trimethylene.

* * * * *